(12) United States Patent
Radigan, II et al.

(10) Patent No.: US 9,963,823 B2
(45) Date of Patent: May 8, 2018

(54) METHODS OF REDUCING THE SIZE OF LIGNOCELLULOSIC MATERIAL, AND RELATED SYSTEMS

(71) Applicant: POET Research, Inc., Sioux Falls, SD (US)

(72) Inventors: Daniel Scott Radigan, II, Sioux Falls, SD (US); James M. Geraets, Sioux Falls, SD (US); Jeffrey R. Heikes, Sioux Falls, SD (US); Rodney Duane Pierson, Dell Rapids, SD (US); David Charles Carlson, Brandon, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days. days.

(21) Appl. No.: 15/153,515

(22) Filed: May 12, 2016

(65) Prior Publication Data
US 2016/0333519 A1   Nov. 17, 2016

Related U.S. Application Data

(60) Provisional application No. 62/161,073, filed on May 13, 2015, provisional application No. 62/161,081, filed on May 13, 2015.

(51) Int. Cl.
| | | |
|---|---|---|
| *D21B 1/04* | (2006.01) | |
| *C12P 19/02* | (2006.01) | |
| *C13K 1/02* | (2006.01) | |
| *C12P 7/10* | (2006.01) | |

(52) U.S. Cl.
CPC .................. *D21B 1/04* (2013.01); *C12P 7/10* (2013.01); *C12P 19/02* (2013.01); *C13K 1/02* (2013.01); *Y02E 50/16* (2013.01)

(58) Field of Classification Search
None
See application file for complete search history.

(56) References Cited

U.S. PATENT DOCUMENTS

| | | |
|---|---|---|
| 4,997,488 A | 3/1991 | Gould et al. |
| 7,189,306 B2 | 3/2007 | Geravis |
| 7,807,419 B2 | 10/2010 | Hennessey et al. |
| 8,852,301 B1 | 10/2014 | Bootsma |
| 9,034,620 B2 | 5/2015 | Narendranath |
| 2009/0053777 A1 | 2/2009 | Hennessey et al. |
| 2010/0129909 A1 | 5/2010 | Stuart |
| 2010/0233771 A1 | 9/2010 | McDonald et al. |
| 2012/0129234 A1 | 5/2012 | McDonald et al. |
| 2013/0065289 A1 | 3/2013 | Carlson |
| 2013/0104880 A1* | 5/2013 | Stuart ...................... C13K 1/02 127/37 |
| 2013/0143290 A1 | 6/2013 | Narendranath |
| 2013/0337521 A1 | 12/2013 | Carlson et al. |
| 2014/0209092 A1 | 7/2014 | McDonald et al. |
| 2014/0234911 A1 | 8/2014 | Narendranath et al. |
| 2015/0037859 A1 | 2/2015 | Bootsma |
| 2016/0121236 A1 | 5/2016 | Carlson et al. |

FOREIGN PATENT DOCUMENTS

| | | |
|---|---|---|
| WO | 2011/028554 A1 | 3/2011 |
| WO | 2012/003310 A1 | 1/2012 |
| WO | 2012/103281 | 8/2012 |

OTHER PUBLICATIONS

Bootsma et al., U.S. Appl. No. 12/827,948, filed Jun. 30, 2010.
Bly et al., U.S. Appl. No. 13/209,170, filed Aug. 12, 2011.
Redford et al., U.S. Appl. No. 15/085,206, filed Mar. 30, 2016.
Redford et al., International Application No. PCT/US16/24946, filed Mar. 30, 2016.
International Search Report and Written Opinion from International Application No. PCT/US2016/032131, dated Sep. 28, 2016 (14 pages).

* cited by examiner

*Primary Examiner* — Mark Halpern
(74) *Attorney, Agent, or Firm* — Kagan Binder, PLLC

(57) ABSTRACT

The present disclosure includes embodiments of methods and systems for reducing the size of lignocellulosic feedstock. The present disclosure also includes embodiments of methods and systems for separating oversized, in process lignocellulosic material, reducing the size of the oversized lignocellulosic material offline, and the reintroducing the lignocellulosic material back into the main process flow after size reduction.

10 Claims, 5 Drawing Sheets

METHODS OF REDUCING THE SIZE OF LIGNOCELLULOSIC MATERIAL, AND RELATED SYSTEMS

RELATED APPLICATIONS

The present non-provisional application claims the benefit of commonly owned provisional applications having Ser. No. 62/161,073, filed on May 13, 2015, and Ser. No. 62/161,081, filed on May 13, 2015, which provisional applications are incorporated herein by reference in their entireties.

FIELD

The present disclosure is related to methods and/or systems for processing lignocellulosic material such as lignocellulosic feedstock. More particularly, the present disclosure is related to methods and/or systems for reducing the size of lignocellulosic material to improve its handleability and processability.

BACKGROUND

Lignocellulosic biomass such as corn cobs and corn stover can be used in a biorefinery to make one or more biochemicals such as ethanol via fermentation.

Prior to fermentation, the biomass can be prepared and processed to release one or more sugars from hemicellulose and/or cellulose. Such processing includes acid hydrolysis, steam explosion, and enzymatic saccharification.

SUMMARY

Disclosed in some embodiments of the present disclosure is a method of processing lignocellulosic feedstock including:
 (a) providing lignocellulosic feedstock having an average length greater than five inches;
 (b) reducing the size of the lignocellulosic feedstock to form a first lignocellulosic material having an average length in the range of from greater than 1 to 5 inches;
 (c) combining the first lignocellulosic material with an aqueous liquid to form a slurry;
 (d) reducing the size of the first lignocellulosic material in the slurry to form a second lignocellulosic material having an average length in the range from greater than 0.5 to 1 inch; and
 (e) reducing the size of the second lignocellulosic material in the slurry to form a third lignocellulosic material having an average length less than 0.5 inches.

Disclosed in some embodiments of the present disclosure is a system for processing lignocellulosic feedstock including:
 (a) a source of lignocellulosic feedstock having an average length greater than five inches;
 (b) a first size reduction device configured to reduce the size of the lignocellulosic feedstock to form a first lignocellulosic material having an average length in the range from greater than 1 to 5 inches, wherein the source of lignocellulosic feedstock is in fluid communication with the first size reduction device;
 (c) a slurry system including:
  i) a vessel configured to receive the first lignocellulosic material and apply an aqueous liquid to the first lignocellulosic material and form a slurry, wherein the vessel is in fluid communication with the first lignocellulosic material and a source of the aqueous liquid; and
  ii) a second size reduction device configured to reduce the size of the first lignocellulosic material in the slurry to form a second lignocellulosic material having an average length in the range from greater than 0.5 to 1 inch, wherein the vessel is in fluid communication with the second size reduction device; and
 (d) a third size reduction device configured to reduce the size of the lignocellulosic material in the slurry to form a third lignocellulosic material having an average length less than 0.5 inches, wherein the vessel or the second size reduction device are in fluid communication with the third size reduction device.

Disclosed in some embodiments of the present disclosure is a method of processing lignocellulosic material including:
 (a) providing a slurry in a first vessel, wherein the slurry includes:
  (i) lignocellulosic material; and
  (ii) an aqueous liquid;
 (b) separating the slurry into a first stream and a second stream, wherein the first stream includes lignocellulosic material having a first average particle size greater than a target value, wherein the second stream includes lignocellulosic material having a second average particle size of the target value or less;
 (c) providing the second stream to a first downstream process;
 (d) reducing the size of the lignocellulosic material from the first stream to form a third stream including lignocellulosic material having a third average particle size, wherein the third average particle size is the target value or less; and
 (e) recycling at least a portion of the third stream to the first vessel and/or providing at least a portion of the third stream to a second downstream process.

Disclosed in some embodiments of the present disclosure is a system for processing lignocellulosic material including:
 (a) a first vessel including a slurry, wherein the slurry includes:
  (i) lignocellulosic material;
  (ii) non-lignocellulosic material selected from the group consisting of dirt, silt, sand, rocks tramp metal, glass, and combinations thereof; and
  (iii) an aqueous liquid;
 (b) a screen device configured to separate the slurry into a first stream and a second stream, wherein the first stream includes lignocellulosic material and non-lignocellulosic material each having a first average particle size greater than a target value, wherein the second stream includes lignocellulosic material having a second average particle size of the target value or less, wherein the first vessel is in fluid communication with the screen device;
 (c) a second vessel configured to separate at least a portion of non-lignocellulosic material from the lignocellulosic material; and
 (d) a size reduction system in fluid communication with the second vessel to receive lignocellulosic material from the second vessel, wherein the size reduction system is configured to reduce the size of the lignocellulosic material into lignocellulosic material having a third average particle size, wherein the third average particle size is the target value or less, wherein the system is configured to recycle at least a portion of the lignocellulosic material to the first vessel and/or to the second vessel and/or a downstream lignocellulosic processing system.

DETAILED DESCRIPTION

Figure 1:
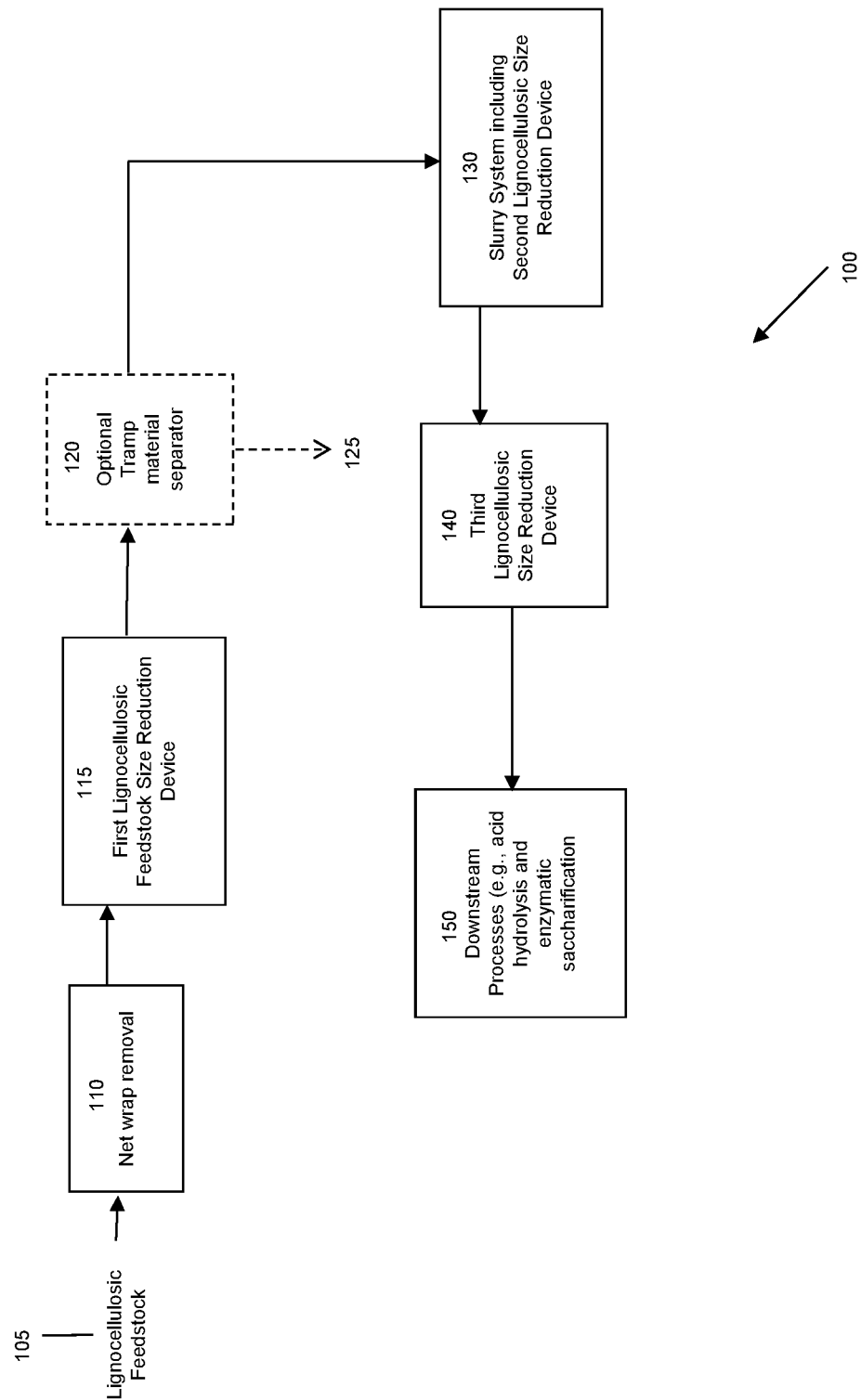
FIG. 1 shows an exemplary embodiment of reducing the size of corn stover feedstock prior to hydrolysis.

The present disclosure includes methods and/or systems to manage lignocellulosic material (e.g., lignocellulosic feedstock) so that it can be more easily handled and processed in a biorefinery, such as a continuous, commercial scale biochemical production facility. One technique relates to processing incoming feedstock in a continuous manner. Another technique can be applied to one or more points throughout a continuous biochemical production process.

Lignocellulosic material can include lignin, hemicellulose, and cellulose. In the context of a biochemical conversion process such as making a biochemical (e.g., ethanol) using a microorganism, a lignocellulosic material can be treated to generate monosaccharides via hydrolysis (acid-catalyzed hydrolysis, enzyme-catalyzed hydrolysis, combinations of these, and the like). In exemplary embodiments, a lignocellulosic material can include corn stover (leaves and stalks and cobs), alfalfa, grasses, soybean stubble, hogged wood, switch grass, *miscanthus*, straw, sawdust, and the like. The monosaccharides can be used by a microorganism (e.g., yeast) to create one or more biochemicals via a biochemical conversion process such as fermentation. The biochemical(s) can be recovered by a variety of techniques such as distillation.

As used herein, "lignocellulosic material" refers to lignocellulosic material that is present at any point in a process of a biorefinery. For example, lignocellulosic material can refer to lignocellulosic material that has been unbaled, ground, pretreated (e.g., with aqueous solutions such as acidic aqueous solutions), steam exploded, saccharified, combinations of these, and the like. In some embodiments, lignocellulosic material includes lignocellulosic feedstock. In some embodiments, at least a portion of the lignocellulosic material has a size that is undesirably too large for handling and processing. As used herein, "feedstock" refers to lignocellulosic material that is minimally processed, if at all, prior to size reduction such as grinding and the like. For example, lignocellulosic feedstock can refer to lignocellulosic material that is in a "green state," which means the feedstock has been recently harvested from a farm or plantation where it was grown. As another example, lignocellulosic feedstock can refer to lignocellulosic material that has been aged (e.g., either in a storage system or in the field where it was grown). Minimal processing that the lignocellulosic feedstock may experience prior to size reduction can include unbaling, cleaning (e.g., to remove dirt and other foreign material), and the like.

A. Reducing the Size of Lignocellulosic Feedstock

A lignocellulosic feedstock can be made available as a source of lignocellulosic feedstock for size reduction. For example, the lignocellulosic feedstock can be transported to a biorefinery in bales or as a loose material. A bale of lignocellulosic feedstock can include bale-wrapping material such as twine, netting, and the like that can wrap around the lignocellulosic feedstock and secure the lignocellulosic feedstock in the form of a bale (e.g., rectangular bale).

If the lignocellulosic feedstock is provided in the form of a bale, the bale can be unbaled prior to size reduction. A bale of lignocellulosic feedstock can be manually unbaled or can be subjected to an unbaling device in an unbaling system to remove the bale-wrapping material such as twine or netting so that the lignocellulosic feedstock is loose enough such that it can be fed to a size reduction device.

As described herein, lignocellulosic feedstock such as corn stover can be reduced in size and into a form that is relatively more can be easy to handle while processing the lignocellulosic feedstock in a biorefinery, especially in a continuous manner. Without appropriate size reduction, lignocellulosic feedstock such as corn stover can be challenging to handle, e.g., in a conveying system, and/or process in a liquid/solid separation system that includes screens, a plate and frame heat exchanger, and the like. Further, it has been discovered that if there are any interruptions or upsets while reducing the size of the lignocellulosic material, the lignocellulosic material remaining in the size reducing device after the "upset" can be oversized to an undue degree and not suitable for use in downstream processes. For example, if solid-liquid separation equipment having screens/filters is used in downstream processing, the screens/filters can become plugged with lignocellulosic material to an undue degree. As another example, plate and frame heat exchangers can have small gaps that become plugged to an undue degree if the lignocellulosic material is not small enough. Embodiments of the present disclosure can overcome these pitfalls.

Embodiments of the present disclosure include reducing the size of a lignocellulosic feedstock to provide a lignocellulosic material (also referred to as a "coarse" size reduction step) followed by forming an aqueous slurry with the lignocellulosic material and performing at least a second and third size reduction to further reduce the size of the lignocellulosic material suitable for subsequent processing such as acid hydrolysis, enzymatic hydrolysis, and the like. The third size reduction can also be referred to as a "fine" size reduction step. In some embodiments, a cleaning step can be performed on the lignocellulosic material between the first and second size reduction steps so as to remove rocks and the like. Advantageously, reducing the size lignocellulosic feedstock such as corn stover according to the methods and systems described herein can make the feedstock relatively more easier to handle and process in a biorefinery.

FIG. 1 shows an exemplary embodiment 100 of the present disclosure illustrating reducing the size of lignocellulosic feedstock.

As shown in FIG. 1, wrapped bales of lignocellulosic feedstock 105 are provided to a net wrap removal system 110. After removing net wrap from bales, whole bales of lignocellulosic feedstock can be fed to a first size reduction device 115 to break up the second-pass bales. The first size reduction device can include a variety of mechanical size reduction devices such a shredder, grinder, and the like. In some embodiments, the first size reduction device can include a twin shaft rotor that shreds the lignocellulosic feedstock to a desirable average length.

After the first size reduction device 115, the average size of the lignocellulosic material (e.g., corn stover) is in a range from 1 to 12 inches, from 1 to 6 inches, from 1 to 5 inches, from 2 to 5 inches, or even from 2.5 to 5 inches.

Optionally, the lignocellulosic material can be cleaned. Cleaning involves removing non-lignocellulosic material from the lignocellulosic material. Exemplary non-lignocellulosic material includes dirt, silt, sand, rocks, tramp metal, glass, and the like. In some embodiments, such cleaning can occur after reducing the size of the lignocellulosic feedstock in the first size reduction device 115, but before forming a slurry with the lignocellulosic material. As shown in FIG. 1, after the first size reduction device 115, the lignocellulosic material can be passed through a separation system 120 to remove the non-lignocellulosic material such as rocks 125 from the lignocellulosic material. A variety of separation systems and devices can be used to separate tramp material from lignocellulosic material. In some embodiments, an air density separation system can be used. In some embodiments, a washing tank that uses gravity to separate tramp material from the lignocellulosic material can be used.

After tramp removal 120, the lignocellulosic material can be provided to (e.g., dropped into) a slurry system 130 where the lignocellulosic material from the first size reduction device can be combined with an aqueous liquid (e.g., water, and optionally with an added acid) to form a slurry in a tank and reduced in size with a second size reduction device. Forming a slurry can help break up clumps of lignocellulosic material and form a pumpable medium for subsequent size reduction and further processing. In some embodiments, the slurry can have a suspended solids level in the range from 5 to 20 percent, 7 to 20 percent, 10 to 18 percent, or even 11 to 17 percent.

A variety of slurry tanks can be used. In some embodiments, a slurry tank having a conveyor mechanism to move material along the bottom to a discharge outlet on a side can be used. An example of conveyor mechanism for inside a slurry tank includes an auger-type device that rotates and applies force to the slurry to move the slurry. In some embodiments, a gravity slurry tank can be used so that at least a portion of the slurry can discharge from the bottom of the tank due to gravity. Further, system 130 includes a second lignocellulosic size reduction device. The second lignocellulosic size reduction device can receive lignocellulosic material in the slurry and reduce it in size so that it has an average length in the range from 0.5 to 1 inch, or even 0.5 to 0.75 inches. The second size reduction device can include a variety of mechanical size reduction devices. In some embodiments, the second size reduction device can include a chopping pump. A chopping pump is a centrifugal pump that is equipped with a cutting system that can macerate solids that are present in the pumped slurry. Chopping pumps are also referred to as a macerator, a shear mixer, etc., and can further reduce the size of the lignocellulosic material in the slurry from the slurry tank.

Advantageously, the second size reduction pump can help stage the size reduction of the lignocellulosic material so that the lignocellulosic material entering the final size reduction device (e.g., the third size reduction device) is relatively more uniform in size and sufficiently small in size so that the final size reduction device is more effective at reducing the size of the lignocellulosic material so that it is within a desired size range exiting the final size reduction device. Without staging the size reduction of the lignocellulosic material in this manner, reducing the size of the lignocellulosic material to within a desired size range can be difficult. In some embodiments, the second size reduction device is configured to pump the slurry at volumetric rate in the range from 1500 to 5000 gallons per minute, or even 2000 to 4000 gallons per minute.

The slurry tank and second size reduction pump can be coupled together in a variety of configurations. Two examples are illustrated with respect to FIGS. 2 and 3.

Figure 2:
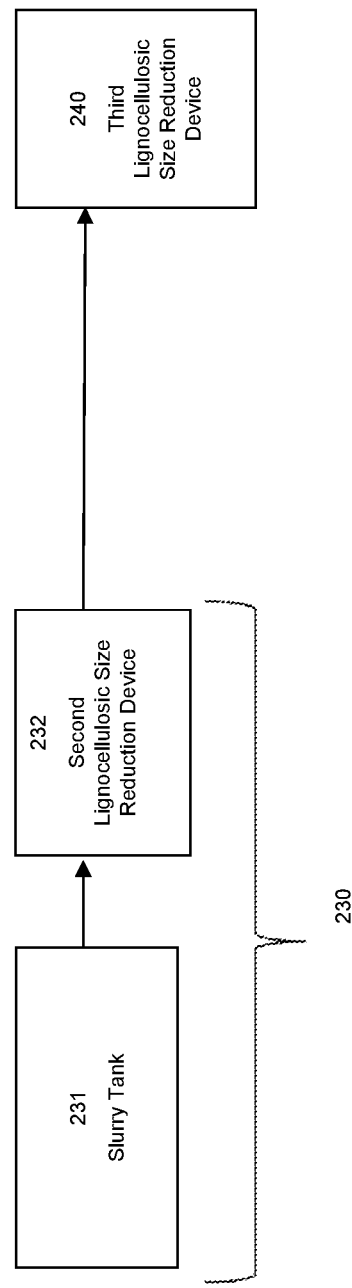
FIG. 2 shows at least a portion of an embodiment of the slurry system shown in FIG. 1.

As shown in FIG. 2, system 230 includes a slurry tank 231 directly coupled to a second size reduction device 232. In some embodiments, slurry tank 232 can be a tank having a conveyor mechanism near its bottom and the second size reduction device 232 can be installed near the outlet of the slurry tank 231 to control the consistency of the slurry at the outlet of tank 231 in order to help keep the outlet stream in a pumpable form that will not plug the equipment and piping. As shown, device 232 can pump the slurry through the downstream in-line third size reduction device 240 (i.e., "fine" grinder).

Figure 3:
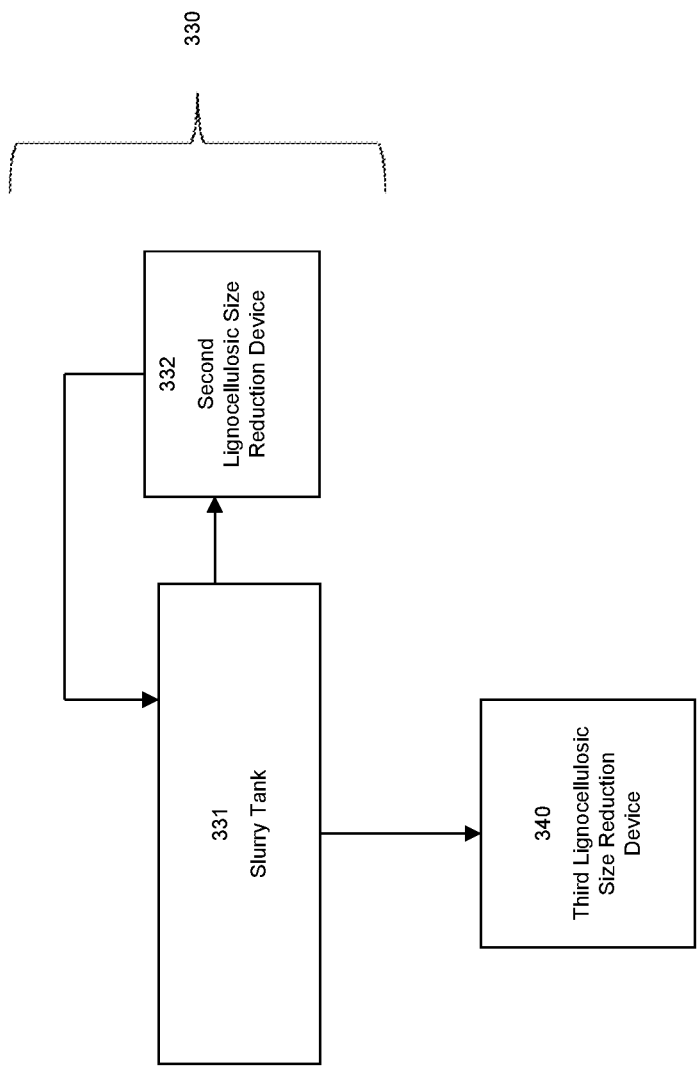
FIG. 3 shows at least a portion of another embodiment of the slurry system shown in FIG. 1.

As shown in FIG. 3, system 330 includes a slurry tank 331 directly coupled to a second size reduction device 332. In some embodiments, slurry tank 332 can be a gravity tank where slurry can discharge from the bottom of the tank 331 due to gravity. As shown the second size reduction device can pump slurry and reduce the size of lignocellulosic material in the slurry and recycle the size reduced material back into tank 331. Size reduction device 332 can help control the consistency of the slurry that is delivered to the downstream in-line third size reduction device 340 (i.e., "fine" grinder). Referring back to FIG. 1, after the slurry system, the slurry including the lignocellulosic material can be pumped to a third lignocellulosic material size reduction device (i.e., a fine grinder) 140. The third size reduction device can help provide the lignocellulosic material with a size that is more handleable and processable in downstream processing equipment. The third size reduction device can include a variety of mechanical size reduction devices such a shredder, grinder, lobe pump, and the like. In some embodiments, the third size reduction device can include a twin shaft rotor that shreds the lignocellulosic material to a desirable average length. In some embodiments, after the third size reduction device 140, the average size of the lignocellulosic material (e.g., corn stover) can be less than 0.5 inches, 0.25 inches or less, 0.2 inches or less, or even 0.1 inches or less. In some embodiments, after the third size reduction device 140, the average length of the lignocellulosic material can be in the range from 0.05 inches to 0.5 inches, from 0.05 inches to 0.5 inches, or even from 0.05 inches to 0.25 inches.

As shown, the slurry from the third size reduction device 140 can either be provided to one or more downstream processes 150 such as acid hydrolysis, enzymatic hydrolysis, fermentation, and the like. Also, if desired, at least a portion of the slurry from third size reduction device 140 can recirculated back to one or more points upstream.

B. Reducing the Size of Lignocellulosic Material

Embodiments of the present disclosure also include separating (e.g., with a gravity screen) oversized lignocellulosic material from a slurry in a process and reducing the size (e.g., grinding) of the oversized lignocellulosic material to within specifications (e.g., offline from the main process flow) and then reintroducing the size-reduced lignocellulosic material back into the main process at one or more points (e.g., recycling upstream to one or more points and/or delivering downstream to one or more points). In some embodiments, the oversized lignocellulosic material can be cleaned to separate dirt, silt, sand, rocks tramp metal, glass, and combinations thereof prior to reducing the size (e.g., grinding or chopping) the oversized lignocellulosic material.

Figure 4:
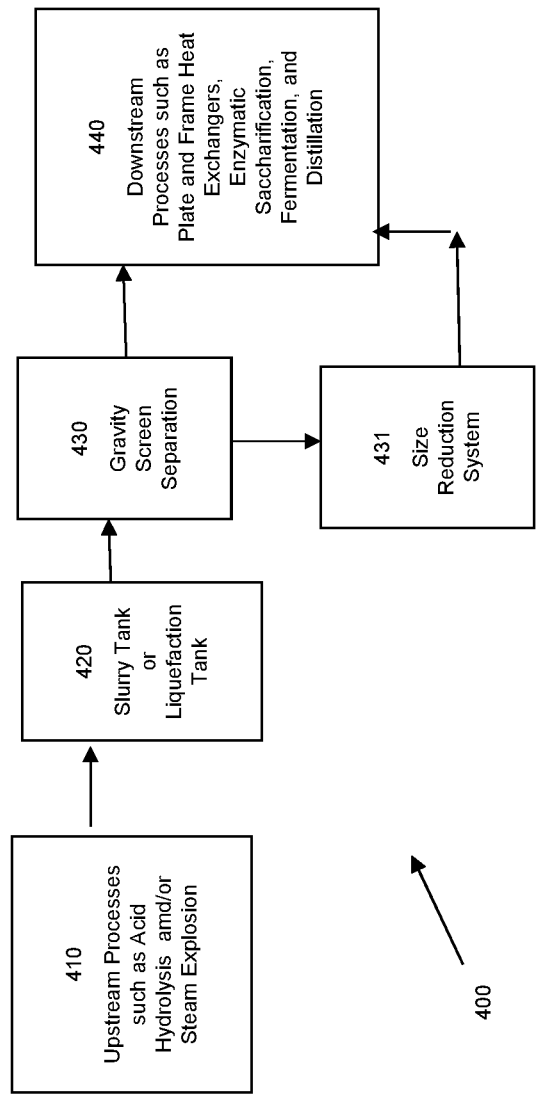
FIG. 4 shows an exemplary embodiment of separating oversized corn stover from a main process stream and reducing the size of the oversized corn stover material offline before reintroducing it back into the main process stream.

FIG. 4 shows an exemplary embodiment 400 of separating oversized lignocellulosic material (e.g., corn stover) from the main process and reducing the size of the oversized material.

As shown in FIG. 4, process 400 can include upstream processes 410 in a lignocellulosic biorefinery configured to make one or more biochemicals such as ethanol. Exemplary upstream processes include one or more of lignocellulosic size reduction, acid hydrolysis, steam explosion, and the like.

As shown in FIG. 4, a slurry from an upstream process 420 such as a slurry tank or a liquefaction tank can be transported and passed (e.g., pumped) through a screening device such as the gravity screen. In some embodiments, corn stover having a size greater than 0.25 inches is separated from the slurry in the gravity screen and taken offline from the main process flow and sent to a size reduction system 431.

The size reduction system 431 can include a "reject" tank and at least one size reduction device to reduce the size of the oversized lignocellulosic material to a desired size. Optionally, liquid can be pumped into the reject tank 535 in order to adjust the consistency of the slurry in the reject tank, or percent of suspended solids by weight, contained in the reject tank. In some embodiments, the slurry in slurry tank 535 can have a suspended solids level in the range from 5 to 20 percent, 7 to 20 percent, 10 to 18 percent, or even 11 to 17 percent.

Figure 5:
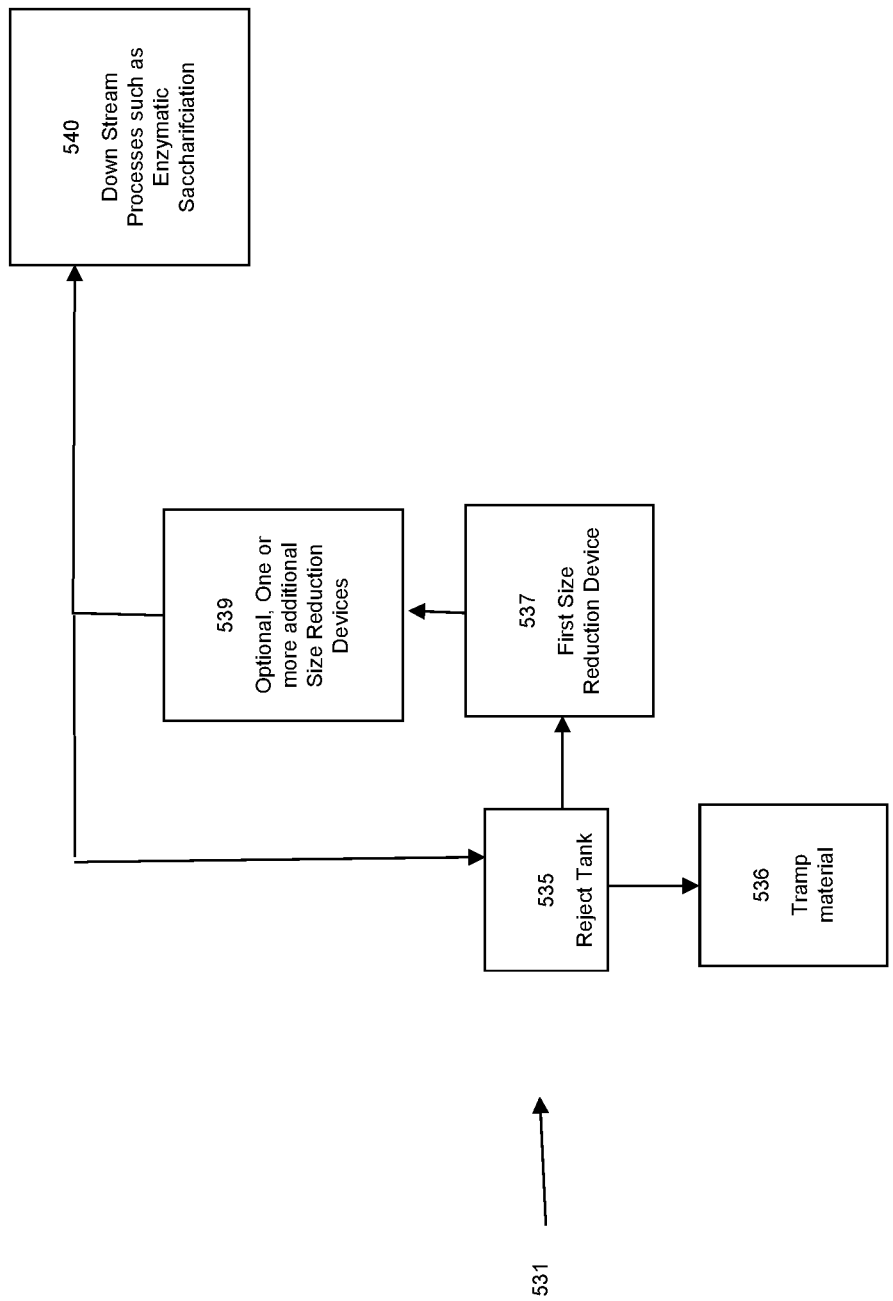
FIG. 5 shows at least a portion of an embodiment of the size reduction system shown in FIG. 4.

The reject tank and at least one lignocellulosic size reduction device can be coupled together in a variety of configurations. One illustrative example is shown in FIG. 5. As shown in FIG. 5, size reduction system 531 includes a reject tank 535. A variety of tanks can be used as a reject tank 535. In some embodiments, a reject tank can have a cone-bottom that can help separate relatively high density solids (rocks, metal, etc.) 536 from relatively low density solids (corn stover, netwrap, etc.). Also, the reject tank 535 can have separate discharges for these two solids streams as shown in FIG. 5. The relatively high density solids 536 can be removed from the bottom of the reject tank 535, while the biomass (corn stover) and liquid can be discharged from the reject tank 535 via a nozzle located just above the cone-bottom section.

As shown in FIG. 5, the biomass, etc. that is discharged via the nozzle can be fed to a first size reduction device 537 to reduce the size of the corn stover to within specification. In some embodiments, the lignocellulosic size reduction device 537 can receive lignocellulosic material in the slurry and reduce it in size so that it has an average particle size of about 0.25 inches or less, 0.2 inches or less, or even 0.1 inches or less. The size reduction device 537 can include a variety of mechanical size reduction devices. In some embodiments, the size reduction device 537 can include a chopping pump. A chopping pump is a centrifugal pump that is equipped with a cutting system that can macerate solids that are present in the pumped slurry. Chopping pumps are also referred to as a macerator, a shear mixer, etc., and can further reduce the size of the lignocellulosic material in the slurry from the slurry tank. The chopping pump can be a non-clogging design to allow the high solids material to be pumped and reduced in size.

Optionally, the size reduction system 531 can include one or more additional size reduction devices 539 as a fail-safe measure in the event that there is an undesirable amount of lignocellulosic material discharged from the size reduction device 537 that is still too large in size. As shown, an additional size reduction device 539 can be directly coupled to the discharge of the chopper pump 537 so that the chopper pump 537 pumps the corn stover material to the device 539, where the solids can be further reduced in size to within specification if necessary. The one or more size reduction devices 539 can include a variety of mechanical size reduction devices such a shredder, grinder, lobe pump, and the like. In some embodiments, the one or more size reduction devices 539 can include a twin shaft rotor that shreds the lignocellulosic material to a desirable average length. In some embodiments, the lignocellulosic size reduction device 539 can receive lignocellulosic material in the slurry and reduce it in size so that it has an average particle size of about 0.25 inches or less, 0.2 inches or less, or even 0.1 inches or less.

As shown in FIG. 5, after the chopper pump 537 and optional device(s) 539, a portion of the stream can be recirculated back to the reject tank 535 for further processing in the size reduction device 537, while a portion of the stream can be reintroduced into downstream processing 540 such as enzymatic saccharification.

Advantageously, methods and systems according to the present disclosure can provide a way to limit the maximum particle size of the corn stover that can get through the slurry system and into downstream processes. For example, plate and frame heat exchangers are often used to cool whole broth after enzymatic saccharification prior to fermentation. If the corn stover is too large in size (e.g., too stringy), the material can plug the gaps in the heat exchangers, which can be as small as 6 to 8 millimeters. Also, methods and systems according to the present disclosure can allow cheaper, more efficient equipment to be used in the downstream processes such as saccharification and fermentation.

What is claimed is:

1. A method of processing lignocellulosic material comprising:
    (a) providing a slurry in a first vessel, wherein the slurry comprises:
        (i) lignocellulosic material; and
        (ii) an aqueous liquid;
    (b) separating the slurry into a first stream and a second stream, wherein the first stream comprises lignocellulosic material having a first average particle size greater than a target value, wherein the second stream comprises lignocellulosic material having a second average particle size of the target value or less;
    (c) providing the second stream to a downstream process;
    (d) reducing the size of the first stream lignocellulosic material to form a third stream comprising lignocellulosic material having a third average particle size, wherein the third average particle size is the target value or less; and
    (e) recycling at least a portion of the third stream to the first vessel.

2. The method of claim 1, wherein the target value is in the range from about 0.01 inches to about 5 inches.

3. The method of claim 1, wherein the target value is about 0.25 inches.

4. The method of claim 1, wherein the first and second downstream process comprises enzymatically saccharifying cellulose that is present in the lignocellulosic material.

5. The method of claim 1, wherein prior to step (b) the slurry has been subjected to a hemicellulose hydrolysis process.

6. The method of claim 1, wherein separating the slurry into a first stream and a second stream comprises passing the slurry through a screen device to separate the slurry into the first stream and the second stream.

7. The method of claim 1, wherein the first stream further comprises non-lignocellulosic material selected from the group consisting of dirt, silt, sand, rocks tramp metal, glass, and combinations thereof, and further comprising, before step (d), providing the first stream into a second vessel that is configured to separate at least a portion of non-lignocellulosic material from the lignocellulosic material.

8. The method of claim 1, wherein the lignocellulosic material comprises corn stover.

9. A method of processing lignocellulosic material comprising:
   (a) providing a slurry feed stream comprising:
      (i) lignocellulosic material; and
      (ii) an aqueous liquid;
   (b) separating the slurry feed stream into a first stream and a second stream, wherein the first stream comprises lignocellulosic material having a first average particle size greater than a target value, wherein the second stream comprises lignocellulosic material having a second average particle size of the target value or less;
   (c) providing the second stream to a downstream process;
   (d) subjecting the first stream to a size reduction operation to form a third stream comprising lignocellulosic material having a third average particle size, wherein the third average particle size is the target value or less; and
   (e) recycling at least a portion of the third stream upstream of step (b).

10. The method of claim 9, further comprising repeating steps (a) through (e) in a continuous operation, wherein the recycled portion of the third stream is combined with slurry feed stream.

* * * * *